(12) United States Patent
Caimmi et al.

(10) Patent No.: US 9,410,941 B2
(45) Date of Patent: Aug. 9, 2016

(54) COMPOSITION FOR THE DETECTION OF ALCOHOL VAPORS IN AN AIR SAMPLE

(71) Applicant: Pietro Caimmi, Bastia Umbra (Perugia) (IT)

(72) Inventors: Pietro Caimmi, Bastia Umbra (IT); Marco Marchetti, Montefiore Dell'Aso (IT); Norberto Roveri, Bologna (IT); Rocco Mercuri, Bevagna (IT); Eros D'Amen, Bologna (IT)

(73) Assignee: CAIMMI, PIETRO, Bastia Umbra (IT)

( * ) Notice: Subject to any disclaimer, the term of this patent is extended or adjusted under 35 U.S.C. 154(b) by 0 days.

(21) Appl. No.: 14/782,680

(22) PCT Filed: Apr. 8, 2013

(86) PCT No.: PCT/IT2013/000100
§ 371 (c)(1),
(2) Date: Oct. 6, 2015

(87) PCT Pub. No.: WO2014/167586
PCT Pub. Date: Oct. 16, 2014

(65) Prior Publication Data
US 2016/0041147 A1  Feb. 11, 2016

(51) Int. Cl.
| | | |
|---|---|---|
| *G01N 33/497* | (2006.01) | |
| *G01N 33/00* | (2006.01) | |
| *G01N 31/22* | (2006.01) | |
| *G01N 33/98* | (2006.01) | |
| *A61B 5/087* | (2006.01) | |
| *G01N 21/78* | (2006.01) | |
| *G01N 33/52* | (2006.01) | |
| *G01N 21/77* | (2006.01) | |
| *A61B 5/08* | (2006.01) | |
| *A61B 5/097* | (2006.01) | |

(Continued)

(52) U.S. Cl.
CPC .......... *G01N 33/4972* (2013.01); *G01N 21/783* (2013.01); *G01N 31/223* (2013.01); *G01N 33/0047* (2013.01); *G01N 33/52* (2013.01); *G01N 33/98* (2013.01); *A61B 5/0452* (2013.01); *A61B 5/082* (2013.01); *A61B 5/097* (2013.01); *A61B 5/4845* (2013.01); *A61K 31/205* (2013.01); *G01N 21/77* (2013.01); *G01N 27/4045* (2013.01); *G01N 31/22* (2013.01); *G01N 2800/307* (2013.01)

(58) Field of Classification Search
CPC ....... G01N 33/98; G01N 21/77; G01N 31/22; G01N 31/223; G01N 21/78; G01N 21/783; G01N 27/4045; G01N 2800/307; G01N 33/497; G01N 33/4972; Y10S 436/90; A61B 5/097; A61K 31/205
See application file for complete search history.

(56) References Cited

U.S. PATENT DOCUMENTS

| | | | | |
|---|---|---|---|---|
| 4,105,409 A | * | 8/1978 | Monnier | G01N 33/98 436/132 |
| 4,492,673 A | * | 1/1985 | Eriksen | G01N 33/98 422/85 |

(Continued)

FOREIGN PATENT DOCUMENTS

| | | |
|---|---|---|
| GB | 1 168 529 A | 10/1969 |
| GB | 1 516 295 A | 7/1978 |

(Continued)

*Primary Examiner* — Jennifer Wecker
(74) *Attorney, Agent, or Firm* — Pearne & Gordon LLP

(57) ABSTRACT

The present invention relates to a silica gel-based composition capable of changing color when placed in contact with alcohol vapors. Said composition is particularly useful for preparing devices for the detection of alcohol, for example devices for carrying out an alcohol test on samples of air exhaled by individuals when subjected to checks by the police or competent authorities.

8 Claims, 2 Drawing Sheets

(51) Int. Cl.
*G01N 27/404* (2006.01)
*A61K 31/205* (2006.01)
*A61B 5/0452* (2006.01)
*A61B 5/00* (2006.01)

(56) References Cited

U.S. PATENT DOCUMENTS 4,789,638 A * 12/1988 Kramer .................. G01N 31/22 422/424

6,479,019 B1 * 11/2002 Goldstein .......... G01N 33/4972 422/83
2007/0258894 A1 * 11/2007 Melker .................. A61B 5/145 424/9.1
2011/0098590 A1 * 4/2011 Garbutt ................ A61B 5/0059 600/532

FOREIGN PATENT DOCUMENTS

| IT | PG20040047 A1 | 1/2005 |
| MX | 9 807 426 A | 3/2000 |

* cited by examiner

COMPOSITION FOR THE DETECTION OF ALCOHOL VAPORS IN AN AIR SAMPLE The present invention relates to a silica gel-based composition capable of changing color when placed in contact with alcohol vapors, usable, for example, for the detection of ethyl alcohol vapors in a sample of air exhaled by a human being.

BACKGROUND ART

An ethylometer is a device for measuring the ethyl alcohol content in the blood, broadly used by law enforcement agencies, above all to check motorists suspected to be in a state of inebriation. This device can comprise a chemical composition capable of changing color in the presence of alcohol vapors. By checking the exhaled breath, in fact, it is possible to understand if an individual has ingested beverages containing ethanol, and whether the intake is higher or lower than the safety values established by the highway code. The operating principle of an ethylometer is based on the fact that, after being ingested, alcohol is rapidly absorbed by the stomach and intestine and is mostly metabolized in the body. A small part, however, is eliminated through urine, sweat and breath. The latter part is what is in practice detected during an alcohol test by means of the composition contained in the ethylometer. Among the common commercially available ethylometers, there exist some of them comprising compositions based on chromium salts, typically dichromate, and/or iodine salts capable of changing color if placed in contact with alcohol vapors.

Patent ITPG20040047, for example, describes in general terms an alcohol testing device which exploits the chromatic properties of a composition comprising an iodine salt, a catalyst in the form of nitrate ions and phosphoric acid- and sulphuric acid-impregnated silica. This mixture, however, requires a laborious and costly process of preparation, which also includes a step of boiling the silica in sulphuric acid.

Moreover, the biggest problem of the compositions generally used in ethylometers is the fact that they are not capable of a long maintaining of the color appearing after the test was performed, and which is indicative of the positive test result. Moreover, the testing rate and the sensitivity to alcohol vapors are often low, so that they are not recommended for a practical and reproducible use.

There thus remains a need to find a composition that is useful for the detection of alcohol vapors in air samples, and which enables the color to be maintained substantially unchanged also for a long time, at the same time ensuring high sensitivity, and rapid response rate.

SUMMARY OF THE INVENTION

The present invention relates, in a first aspect, to a composition for the detection of alcohol vapors in an air sample, said composition comprising:
at least one hepta- or pentavalent iodine salt, silica gel, sulphuric acid, and
characterized in that it further contains nitrate ions in an amount comprised between 2.5 and 10% by weight.

In a further aspect, the invention relates to a process for preparing the composition, said process comprising the dry mixing of the silica with a penta- or hepta-valent iodine salt, followed by the contact with a solution of a nitrate salt in sulphuric acid.

An additional aspect is the use of the present composition for detecting the presence of alcohol vapors, preferably ethyl alcohol vapors ($CH_3CH_2$—OH), in air samples, for example samples of air exhaled by human beings or air samples drawn from closed environments.

Alcohol vapors can be detected for an alcohol content expressed by ethanol which ranges from 0.01, or even less, to about 2 g/L.

In another aspect, the invention relates to a method for the detection of alcohol vapors in the air which comprises placing the present composition in contact with an air sample, and observing the color change, if any.

Finally, additional aspects of the invention are: a container comprising the present composition, preferably in the form of a vial; and
a device for carrying out the above-described method, preferably in the form of an ethylometer.

DETAILED DESCRIPTION

Figure 1A:
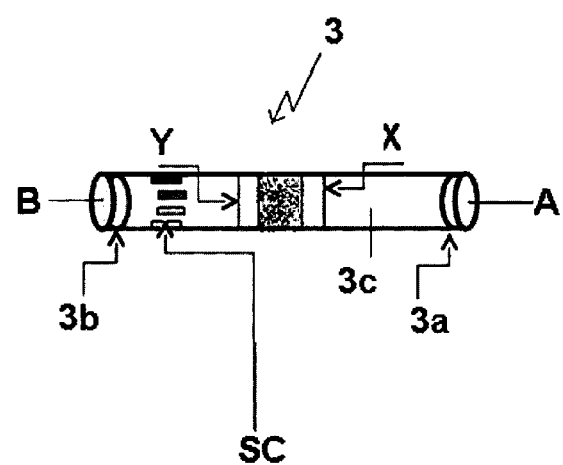
FIG. 1a schematically represents a container 3 in the form of a cylindrical vial, upon whose outer surface there is a color scale for measuring the corresponding alcohol content.

Unless otherwise specified, the percentages by weight of the components are understood as amounts of the component considered, relative to the total weight of the mixture. The term "alkali" or "alkaline earth" metal means a metal of the first or second group of the periodic table, e.g. potassium, sodium, magnesium, calcium and the like. The term "penta-" or "hepta-" valent iodine is intended to indicate, respectively, iodine having an atomic number of 5+ or 7+. Therefore, the compounds comprising said ions, according to the present invention, are understood as salts of the iodate ($IO_3^-$) and periodate ($IO_4^-$) ions, as described below in detail.

The composition of the invention is capable of changing color if placed in contact with an air sample containing alcohol vapors, turning from an initially whitish color into a pink-violet color. Practically speaking, in a normal condition (i.e. in the absence of alcohol vapors) the composition has a whitish color, due to the presence of silica gel as the main component. In the presence of alcohol vapors, on the other hand, the composition takes on a pink-violet color, caused by an oxidation-reduction process between the iodine and ethyl alcohol. When the composition is in contact with alcohol vapors, for example present in a sample of air exhaled by a person, or an air sample from an industrial environment, the iodine having an oxidation number of +5 or +7, is reduced to elementary iodine $I_2$ (i.e. with an oxidation number equal to 0), imparting a characteristic violet-pink color to the composition. In the absence of such alcohol vapors, the iodine is not reduced and the composition maintains its whitish color. The intensity of the color is directly proportional to the amount of alcohol vapors actually present in the analyzed air.

Thanks to its chromatic properties, the composition can be conveniently used, for example, to carry out so-called "alcohol tests", generally used by the police and law enforcement agents to determine the percentages of ethyl alcohol present in the blood of a driver. By the contact with a sample of air exhaled by a driver in a state of inebriation, the pink-violet color taken on by the present composition can be indicative of the presence of a certain quantity of alcohol in the individual's breath and hence blood.

As mentioned above, the composition contains silica, sulphuric acid and penta- or hepta-valent iodine salts and it is characterized in that it contains a specific amount of nitrate ions, intended as $NO_3^-$ ions, typically present as nitrate salts.

In addition to the amount of nitrate ions, the present composition for the detection of alcohol vapors in the air is further characterized in that it does not contain phosphoric acid or chromium salts, unlike similar compositions used in the art for this purpose.

Therefore, in one embodiment, the invention relates to a composition, understood as being free of phosphoric acid and/or chromium salts, which consists in:
at least one salt comprising hepta- or penta-valent iodine, silica gel,
sulphuric acid, and
nitrate ions in a concentration comprised between 2.5 and 10% by weight.

The composition preferably comprises hepta- or penta-valent iodine salts of the iodate ($IO_3^-$) or periodate ($IO_4^-$) type of alkali or alkaline earth metals, preferably selected from: potassium, sodium and cesium.

In a preferred embodiment, the composition comprises iodate salts of alkali or alkaline earth metals, even more preferably selected from among: potassium iodate ($KIO_3$), sodium iodate ($NaIO_3$) and cesium iodate ($CsIO_3$), $KIO_3$ being particularly preferred.

The hepta- or penta-valent iodine salts can be used in amounts by weight comprised between 1 and 10%, preferably comprised between 1.5 and 7%.

The silica (or silica gel) is the one commonly used in chemistry, having the general formula $SiO_2$ and readily available in the market at a low cost. As may be inferred from the present description, in the composition of the invention the silica used as a substrate material is non-impregnated silica, unlike the silica used in the prior art, which is usually pretreated with an acid boiling treatment. In other words, the silica of the present composition does not undergo any pretreatment with acidic or alkaline substances. This has numerous implications and practical advantages, including that of avoiding costly and potentially dangerous steps of impregnation with acids, and above all that of being able to use an not-impregnated substrate (silica) which is thus capable of absorbing and rendering visible even small percentages of red iodide vapors, eventually appearing upon contact with alcohol vapors.

The present composition is in fact endowed with a high sensitivity, being capable of detecting percentages of alcohol vapors that are even lower than 0.5 g/l, indeed even lower than 0.2 g/l, for example 0.1 g/l. Different particle sizes of silica can be used, for example comprised between 0.4 and 2, generally in amounts by weight comprised between 75 and 98% depending, for example, on the type of device intended to be developed to carry out the alcohol test.

The sulphuric acid ($H_2SO_4$) present in the composition of the invention is generally concentrated sulphuric acid, i.e. having a concentration comprised between 95 and 98%, or even oleum, i.e. the so-called "fuming" sulphuric acid, obtainable, for example, by mixing sulphur trioxide and sulphuric acid. Preferably, 98% concentrated sulphuric acid is used. In one embodiment, the acid is in an amount comprised from 10 and 50%, more preferably comprised from 12 and 40%. Besides sulphuric acid, the present composition does not contain any additional acids, such as, for example, phosphoric acid, as occurs in the prior art.

As regards the nitrate ions, these can be present both as salts with an alkali or alkaline earth metal, or also as an ammonium salt. Preferably, the composition comprises: ammonium nitrate ($NH_4NO_3$), or potassium, sodium or cerium nitrate, potassium or cerium nitrate being particularly preferred.

The selected salt is used in an amount preferably comprised between 4% and 10%, even more preferably comprised between 5% and 7%. Larger percentages would lead to a saturation of the solution with nitrate ions, which would inhibit the reaction, since they would re-crystallize, going to form crystals on the surface of the silica gel grains and thereby creating a barrier to the alcohol vapors, which would not be detected.

Surprisingly, the present composition makes it possible not only to obtain excellent results in terms of sensitivity to alcohol vapors, but also to maintain the color after contact with said vapors, even for a long time. In this regard it should be noted that the present composition is in fact capable of maintaining the color taken on at the end of the test even for 2 or 3 days. This is particularly advantageous above all when the composition is used in a device to measure the concentration of ethyl alcohol in a breath sample, and hence in the blood of a vehicle driver. As a result, the test can be used as evidence in any situations in which a decision must be made a posteriori. This property of long duration of the color is probably due to the fact that since the silica is used in a not impregnated form, it is capable of trapping and holding the iodide ions that are formed by the reduction of the penta-or heptavalent iodine ions upon contact with the alcohol vapors.

Furthermore, the present composition is capable of showing the pink-violet color in a very short time, even instantly upon contact with the air to be analyzed. This latter property is likewise attributable to the fact that the silica used is silica that is not treated, but rather dry functionalized. Thanks to this, in fact, the oxidation-reduction reaction between iodine and ethyl alcohol occurs on the surface of the grains and not inside the pores in case created by an acid pre-treatment, unlike in prior art devices, which can require times of response sometimes even longer than one minute.

Therefore, an additional aspect of the invention is the use of the present composition for detecting the presence of alcohol vapors, preferably ethanol or ethyl alcohol ($CH_3CH_2$—OH) vapors, in air samples. The latter can be samples of air exhaled by human beings or drawn from closed environments, such as laboratories or rooms, as well as reactors, silos and the like.

The present invention also relates to a process for preparing the above-described composition, said process comprising the steps of:
 a) dry mixing the non-impregnated silica with a penta- or hepta-valent iodine salt, and
 b) placing the mixture thus obtained in contact with a solution of a nitrate salt in concentrated sulphuric acid.

The mixing step a) can take place with the use of known machinery or devices for dry mixing two solid components, such as, for example, mills, mixers, homogenizers, blade stirrers and the like.

The iodine salts are periodate or, preferably, alkali or alkaline earth metal iodate salts as defined above in detail, sodium and potassium salts being particularly preferred.

The mixing of the two components takes place in a short time, i.e. comprised between a few minutes and about an hour, typically depending on the amount of material to be mixed and the type of machinery used. In general, however, it does not take longer than 1.5-2 hours to carry out step a).

After the preparation of the silica-iodine salt mixture, the latter is placed in contact, according to step b), with a solution of concentrated sulphuric acid or sulphuric acid in the form of oleum in which nitrate salt has been dissolved, in accordance with the preceding embodiments. In this regard, the acidic solution that is obtained has a nitrate ion concentration preferably comprised between 4 and 10% relative to the weight of the silica. The contact between the solid mixture and the acidic solution preferably occurs by diffusion at ambient temperature (i.e. comprised between around 5 and 40° C.) or also at higher temperatures, i.e. up to around 70° C., for a time which can range from a few minutes to a few hours, for example between 5 and 60 minutes.

At the end of step b) the composition is completely dried, generally using methods known to the person skilled in the art, and can be conveniently stocked and/or stored, preferably in moisture-tight containers. The composition can also be advantageously packed directly in ready-to-use containers, for example in the form of vials or the like. As may also be inferred from the experimental part herein included, the preparation of the mixture takes place in an extremely simple and highly reproducible manner, without envisaging any step of impregnation of the silica, or any acid pre-contact. This makes it possible on the one hand to increase the safety of the entire process, and on the other hand to considerably optimize the times of preparing the final product.

A further aspect of the invention is a method for the detection of alcohol vapors in the air which comprises placing the present composition in contact with an air sample and observing whether there is any color change. The present method can be conveniently used to analyze samples of air exhaled by a human being or air samples drawn from closed environments or rooms in which one wishes to detect, for example for safety reasons, the presence of alcohol vapors. When the present method is used to carry out an alcohol test on a human being, the composition is used as the main component of devices such as ethylometers or the like, whereas in the latter case, the composition of the invention can be included in special containers of various sizes, and with characteristics depending, for example, on the type of room or the amount of composition one wishes to use. Examples of such closed environments or rooms are laboratories in general, or also reactors or industrial silos, whereby it is often necessary to check the formation of toxic or potentially dangerous gases.

An additional aspect of the invention is a device for carrying out an alcohol test 1, comprising a container 3 containing the present composition, connected to a mouthpiece 2 and a bag 4.

The container 3, is preferably in the form of a cylindrical vial and is made with a transparent polymeric material such as polycarbonate, unexpanded polystyrene, polystyrene or glass. In one embodiment, the container is rendered antibacterial, or even biodegradable, using specific masterbatches known in the art for such purposes.

Figure 1B:
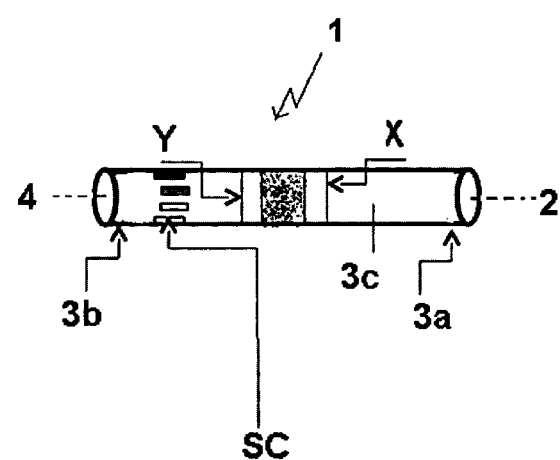
FIG. 1b schematically represents a device 1 for the detection of ethyl alcohol vapors (ethylometer) according to the present invention.

The container 3 is configured in such a way as to be able to be connected by means of a first end 3a and a second end 3b respectively to a mouthpiece 2 and to a bag 4, thereby forming the device for measuring alcohol content (ethylometer), as illustrated, for example, in figure 1b. In this manner the mouthpiece 2 is in fluid communication with the inside of the container, and the container 3 is in turn in communication with the bag 4.

FIG. 1a shows a schematic representation of the container 3, in cylindrical form, on the surface of which there is indicated a color scale SC, useful for determining the value of the alcohol present in the air sample and corresponding to the color taken on by the composition of the invention. Typically, the container comprises the composition of the invention inserted inside two filters x and y.

Said container 3 generally comprises connection means disposed at the two end sides to make said connection. In a preferred embodiment, said means are snap-fit or screw-type means.

In a preferred embodiment, the container 3 contains the composition of the invention in an inert gas atmosphere. Practically speaking, the container is filled with the composition, and then an inert gas, preferably nitrogen or argon, is blown in. In this manner, the composition will show improved stability over time, thus assuring a longer storage life. As indicated in figure 1a, typically in order to better preserve the inert environment, the cartridge can be stored in a closed form, i.e. by closing off its ends, for example, with plastic caps A and B.

In this regard, therefore, the invention relates to a device capable of detecting the presence of ethyl alcohol vapors in an air sample (ethylometer) which comprises the above-described container 3, to whose first end 3a and second end 3b the mouthpiece 2 and the bag 4 are respectively connected, as illustrated, for example, in FIG. 1b.

The mouthpiece 2, generally cylindrical in shape, is preferably made of an antibacterial polymeric material. It is configured in such a way as to be able to be connected to the container 3 directly or also by means of interposed fluid connection means. During use, the mouthpiece conveys the air exhaled by the individual into the vial, so that the air is in contact with the composition of the invention, which will change color according to the percentage of any alcohol vapors present in the exhaled air.

As mentioned above, the second end 3b of the vial is connected to a bag 4, typically based on a plastic material commonly used, for example, in the realm of healthcare. Preferably, said bag has a volume of about 1-1.2 liters, even more preferably about 1 liter.

Using the present device 1, when the exhaled air is placed in contact with the present composition inside the vial (by means of the mouthpiece) and subsequently collected (in the bag) after passing through the composition itself, if ethanol vapors are present a change in the color of the composition will be observed, depending on the amount of ethanol present in the air.

In this regard, by comparing it with a color scale SC, which goes from white to dark violet, it will be possible to determine the percentage of alcohol content detected. The color scale in fact shows a series of intermediate colors that go gradually from white (i.e. absence of ethanol) to dark violet (i.e. presence of a percentage of alcohol of about 2%), which are associated with the corresponding alcohol concentrations detected by the composition.

In a preferred embodiment, and as indicated, for example, in FIG. 1a, said color scale SC is positioned on the outer surface of the container 3c, for example as an adhesive label, or also printed directly onto the outer surface of the container itself. Alternatively, or in addition, said scale can also be pre-printed on another support (for example cardboard or plastic), and used after the individual has blown into the mouthpiece in order to identify the percentage of alcohol associated with the color taken on by the composition inside the transparent vial.

Furthermore, the ethylometer 1 of the invention can be conveniently assembled in a 5-part kit which comprises: the container 3, preferably in the form of a vial, as described above in detail, a mouthpiece 2 and a bag 4, and optionally a support made, for example, of cardboard or plastic, on which the color shades from white to dark violet, associated with corresponding values of alcohol content, are printed.

Said kit 5 can contain the three components 2,3,4 in three separate compartments, in partial combination with each other (for example container and mouthpiece or container and bag) or also, preferably, in a single one.

The present invention will now be described with examples that are not intended in any way to limit the scope hereof.

EXPERIMENTAL PART

Example 1

Use of the Composition in the Detection of Ethyl Alcohol Vapors

Air samples comprising respectively an amount of alcohol vapors equal to: 0.1, 0.5, 0.8, 1.0, 1.2 and 1.5 g/l are placed in contact with a composition of the invention comprising:

5% potassium iodate,
4% potassium nitrate
91% silica gel, with a particle size of 0.4-0.7, using a pump or the calibrated bag contained in the kit of the invention.

In the space of a few seconds the composition, initially white, takes on a pink-violet color, indicative of the presence of alcohol vapors.

This color is also checked at intervals of approximately 30 minutes following the color change and significant persistence of color may be noted throughout the next 3 hours.

Example 2

Preparation of the Composition of the Invention

A silica/$KIO_4$ mixture is prepared by weighing 100 g of sieved silica gel with a suitable particle size and adding 5 g of $KIO_4$, followed by stirring.

A mixture with 20 g of $H_2SO_4$ and 7 g of $KNO_3$ is prepared separately.

The latter mixture is added to the above-described silica/$KIO_4$ mixture, and then follows another 10 minutes of stirring.

The invention claimed is:

1. A process for the preparation of a composition for the detection of alcohol vapors in an air sample, comprising the following steps:
   (a) dry mixing a hepta- or penta-valent iodine salt with silica gel;
   (b) contacting the result of step (a) with a solution of a nitrate salt in sulphuric acid, and thereafter yielding the composition.

2. The process of claim 1, wherein the composition contains nitrate ions in a concentration between 2.5% and 10% by weight.

3. The process of claim 1, wherein said hepta- or penta-valent iodine salt is an iodate or periodate salt of an alkali or alkaline earth metal.

4. The process of claim 3, wherein said alkali or alkaline earth metal is selected from the group consisting of potassium, sodium and cesium.

5. The process of claim 1, wherein the composition contains nitrate ions in a concentration between 5% and 10% by weight.

6. The process of claim 1, wherein the composition contains nitrate ions in a concentration between 5% and 7% by weight.

7. The process of claim 1, wherein the nitrate salt is a nitrate salt of an alkali or alkaline earth metal or of ammonium.

8. The process of claim 1, wherein said nitrate salt is selected from the group consisting of potassium nitrate, ammonium nitrate and cesium nitrate.

* * * * *